(12) United States Patent
Sunagawa et al.

(10) Patent No.: US 8,790,253 B2
(45) Date of Patent: Jul. 29, 2014

(54) LIGHT SOURCE DEVICE, IMAGING APPARATUS AND ENDOSCOPE APPARATUS

(75) Inventors: Hiroshi Sunagawa, Kanagawa (JP); Akira Mizuyoshi, Saitama (JP)

(73) Assignee: Fujifilm Corporation, Tokyo (JP)

( * ) Notice: Subject to any disclaimer, the term of this patent is extended or adjusted under 35 U.S.C. 154(b) by 1336 days.

(21) Appl. No.: 12/484,198

(22) Filed: Jun. 13, 2009

(65) Prior Publication Data

US 2009/0312607 A1 Dec. 17, 2009

(30) Foreign Application Priority Data

Jun. 13, 2008 (JP) ................................ 2008-156032

(51) Int. Cl.
*A61B 1/06* (2006.01)
*A61B 1/07* (2006.01)

(52) U.S. Cl.
CPC ............ *A61B 1/06* (2013.01); *A61B 1/0638* (2013.01); *A61B 1/0653* (2013.01); *A61B 1/07* (2013.01); *A61B 1/0661* (2013.01)
USPC ........... 600/180; 600/178; 600/182; 600/160; 600/109; 362/84; 362/574; 362/551; 362/227; 362/260

(58) Field of Classification Search
CPC ...... A61B 1/06; A61B 1/0638; A61B 1/0653; A61B 1/0661; A61B 1/07
USPC ............. 600/178, 179, 181, 182; 362/84, 574
See application file for complete search history.

(56) References Cited

U.S. PATENT DOCUMENTS

| 4,821,117 A | 4/1989 | Sekiguchi |
| RE34,411 E * | 10/1993 | Nishioka et al. ................ 348/70 |
| 5,420,080 A | 5/1995 | Wang et al. |

(Continued)

FOREIGN PATENT DOCUMENTS

| DE | 10 2006 053487 A | 5/2008 |
| EP | 1 575 423 A | 9/2005 |

(Continued)

OTHER PUBLICATIONS

Trials for development and clinical application of an electronic endoscope system having a built-in narrow band filter (Narrow Band Imaging: NBI) (Yasushi Sano, Shigeaki Yoshida (National Cancer Center East Hospital), Masahiko Kobayashi (Self-Defense Forces Central Hospital), GastroenterolEndosc, Sep. 20, 2000.). Translation provided.

(Continued)

*Primary Examiner* — John P Leubecker
*Assistant Examiner* — Arnaldo Torres Diaz
(74) *Attorney, Agent, or Firm* — McGinn IP Law Group, PLLC

(57) ABSTRACT

A light source device includes a first light source, a second light source having an emission wavelength that is different from the first light source, and a phosphor that is disposed to be distant from the first light source and the second light source and absorbs light in a predetermined excitation wavelength band to emit fluorescence. The phosphor is disposed on an emission light optical path that is shared by the first light source and the second light source. The emission wavelength of the first light source is in the predetermined excitation wavelength band. The emission wavelength of the second light source is outside of the predetermined excitation wavelength band.

13 Claims, 12 Drawing Sheets

(56) References Cited

U.S. PATENT DOCUMENTS

| | | | |
|---|---|---|---|
| 5,439,616 A | 8/1995 | Ishiwata et al. | |
| 5,545,595 A | 8/1996 | Wang et al. | |
| 6,350,041 B1 | 2/2002 | Tarsa et al. | |
| 6,602,186 B1 | 8/2003 | Sugimoto et al. | |
| 7,020,378 B2 | 3/2006 | Poisel et al. | |
| 7,179,222 B2* | 2/2007 | Imaizumi et al. | 600/109 |
| 7,187,453 B2* | 3/2007 | Belleville | 356/504 |
| 7,235,045 B2 | 6/2007 | Wang et al. | |
| 7,330,205 B2 | 2/2008 | Hakamata | |
| 7,892,169 B2* | 2/2011 | Gono et al. | 600/178 |
| 8,197,111 B2 | 6/2012 | Hama et al. | |
| 2003/0007087 A1* | 1/2003 | Hakamata et al. | 348/370 |
| 2004/0148141 A1* | 7/2004 | Tsujita et al. | 702/190 |
| 2005/0027166 A1* | 2/2005 | Matsumoto et al. | 600/162 |
| 2005/0124858 A1 | 6/2005 | Matsuzawa et al. | |
| 2005/0288553 A1* | 12/2005 | Sugimoto | 600/118 |
| 2006/0017913 A1 | 1/2006 | Kawamata et al. | |
| 2006/0149133 A1 | 7/2006 | Sugimoto et al. | |
| 2006/0152926 A1 | 7/2006 | Hama et al. | |
| 2006/0173245 A1 | 8/2006 | Todd et al. | |
| 2006/0235277 A1* | 10/2006 | Ohkubo et al. | 600/179 |
| 2007/0149858 A1 | 6/2007 | Ogawa et al. | |
| 2007/0213592 A1* | 9/2007 | Yamada | 600/178 |
| 2007/0297190 A1 | 12/2007 | Ng | |
| 2008/0039696 A1* | 2/2008 | Kamihara | 600/181 |
| 2008/0039697 A1* | 2/2008 | Morishita | 600/181 |
| 2008/0051632 A1* | 2/2008 | Ito et al. | 600/114 |
| 2008/0089089 A1 | 4/2008 | Hama et al. | |
| 2008/0205477 A1 | 8/2008 | Hama et al. | |
| 2008/0239070 A1* | 10/2008 | Westwick et al. | 348/68 |
| 2009/0040598 A1 | 2/2009 | Ito | |
| 2009/0065679 A1* | 3/2009 | Tanimoto | 250/208.1 |
| 2009/0167149 A1 | 7/2009 | Ito | |
| 2009/0194699 A1 | 8/2009 | Smitt et al. | |
| 2009/0306478 A1 | 12/2009 | Mizuyoshi | |
| 2010/0016669 A1* | 1/2010 | Takaoka et al. | 600/160 |
| 2010/0094136 A1* | 4/2010 | Nakaoka et al. | 600/477 |
| 2010/0256504 A1* | 10/2010 | Moreau-Gaudry et al. | 600/476 |

FOREIGN PATENT DOCUMENTS

| | | |
|---|---|---|
| EP | 1 787 571 A | 5/2007 |
| EP | 1 795 798 A | 6/2007 |
| EP | 1 867 272 A | 12/2007 |
| EP | 2 026 108 A | 2/2009 |
| JP | SHO. 60-225820 A | 11/1985 |
| JP | HEI. 6-40174 B | 5/1994 |
| JP | HEI. 7-69673 A | 3/1995 |
| JP | HEI. 7-97572 A | 4/1995 |
| JP | 2641653 B2 | 5/1997 |
| JP | 10-243915 A | 9/1998 |
| JP | 2001-170009 A | 6/2001 |
| JP | 2003-61909 A | 3/2003 |
| JP | 2005-106801 A | 4/2005 |
| JP | 2005-198794 A | 7/2005 |
| JP | 2005-205195 A | 8/2005 |
| JP | 2005-328921 A | 12/2005 |
| JP | 2006-002115 A | 1/2006 |
| JP | 2006-61685 A | 3/2006 |
| JP | 2006-68488 A | 3/2006 |
| JP | 2006-166940 A | 6/2006 |
| JP | 2006-173324 A | 6/2006 |
| JP | 2006-288535 A | 10/2006 |
| JP | 2006-296656 A | 11/2006 |
| JP | 2007-95809 A | 4/2007 |
| JP | 2007-111151 A | 5/2007 |
| WO | WO 2006/038502 A1 | 4/2006 |

OTHER PUBLICATIONS

Phosphor for White LED, Tsutomu Odaki, IEICE Technical Research Report ED2005-20, CFM2005-28, SDM2005-28, pp. 69-74 (May 2005). Partial translation provided.
New SiALON phosphors and white LEDs, Naoto Hirosaki, Xie Rong Jun and Ken Sakuma, Transactions of JSAP, vol. 74, No. 11, pp. 1449-1452 (2005). Partial translation provided.
Present status and prospect of multinary phosphor materials, Hajime Yamamoto, School of Bionics, Tokyo University of Technology, Transactions of JSAP, vol. 76, No. 3, p. 241 (2007). Partial translation provided.
European Search Report dated Sep. 2, 2009.
European Search Report dated Sep. 21, 2010.
Extended European Search Report issued on Aug. 25, 2009, replaced EESR issued on Oct. 5, 2009.
United States Office Action dated Mar. 30, 2012, in U.S. Appl. No. 12/837,124.
United States Office Action dated Mar. 26, 2012, in U.S. Appl. No. 12/478,704.
Japanese Office Action dated Sep. 4, 2012, with English translation.
Japanese Office Action dated Sep. 25, 2012, with English translation.
Japanese Office Action dated Oct. 30, 2012 with partial English translation thereof.
Japanese Office Action dated Nov. 13, 2012, with English translation.
European Search Report dated Aug. 20, 2012.
European Office Action dated Feb. 13, 2014.

* cited by examiner

FIG. 10A
FIG. 10B
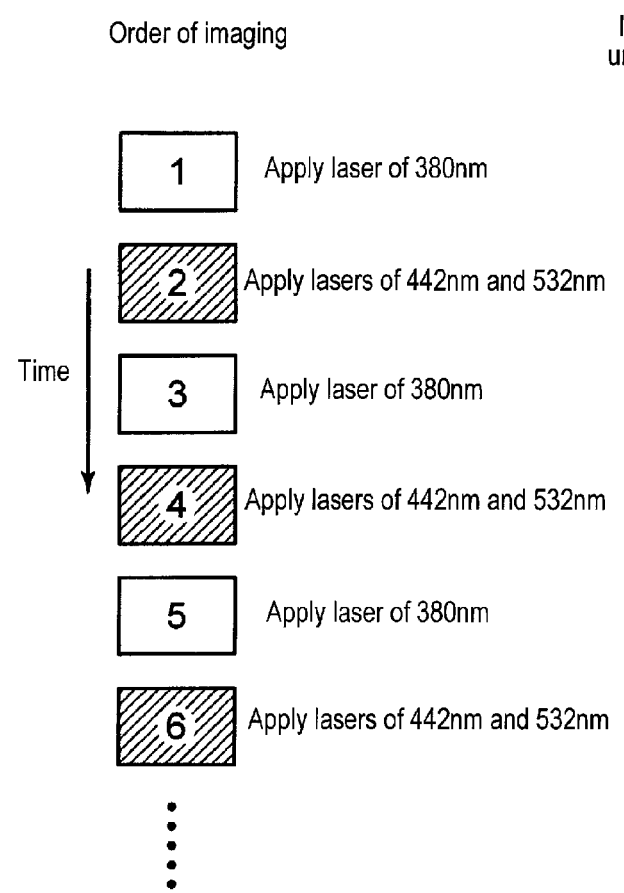
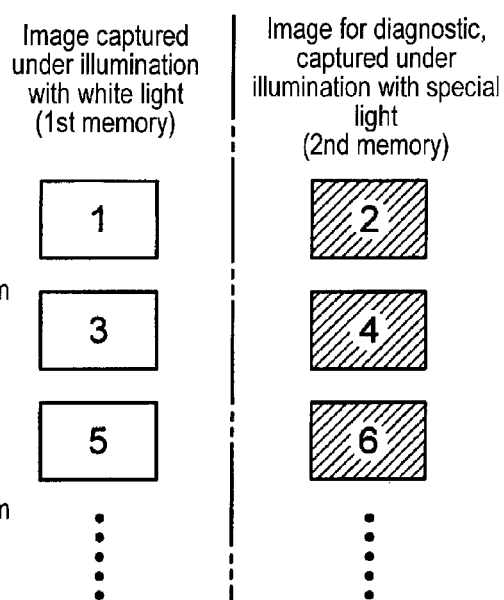

LIGHT SOURCE DEVICE, IMAGING APPARATUS AND ENDOSCOPE APPARATUS

CROSS-REFERENCE TO RELATED APPLICATIONS

This application claims the benefit of Japanese Patent Application No. 2008-156032, filed Jun. 13, 2008, the entire contents of which are hereby incorporated by reference, the same as if set forth at length.

BACKGROUND OF THE INVENTION

1. Technical Field

The invention relates to a light source device, an imaging apparatus and an endoscope apparatus.

2. Description of the Related Art

An endoscope apparatus that has been widely used is configured so that illumination light from a lamp that is provided in a light source device is guided by a light guide that is provided along an endoscope insertion portion, and the illumination light guided by this light guide is emitted from an illumination window that is provided at a front end of the endoscope insertion portion so as to illuminate an object site to be inspected. On the other hand, JP 2005-205195 A describes a light source device in which a blue laser beam is guided to a front end side of an endoscope insertion portion by an optical fiber, and a phosphor disposed at a front end of the optical fiber is excited by the blue laser beam to emit light and irradiate white illumination light. Since this light source device has an outer diameter that is narrower than a fiber bundle of the related art, this light source device can be suitable for use in the case where an endoscope is required to have a narrow outer shape as in a transnasal endoscope. However, in this case, the illumination light runs short of an intensity of light around 450 to 480 nm and thus is poor in color rendering property as compared to a continuous spectrum, over a wavelength 430 to 680 nm, of an illumination light (Xe lamp), of the related art, for an endoscope.

Also, in an endoscopic diagnosis, there is a method called a special light diagnosis utilizing an image obtained by illuminating with light in a specific wavelength band, in addition to observation by using the white illumination light (see JP 2001-170009 A and JP 2005-198794 A, for example). In those cases, light in a specific narrow wavelength band is employed as illumination light. The special light diagnosis, for example, can clearly observe a nascent blood vessel produced in a mucosal layer or a mucosal underlying layer, and also can depict the fine structure of a mucosal surface that cannot be obtained in an ordinary observation image. Therefore, this special light diagnosis is beneficial for a diagnosis of lesion, an early detection of cancer, and the like.

Meanwhile, in order to emit light in a specific wavelength band for the special light diagnosis in addition to white illumination light that is obtained by a combination of the laser beam and the phosphor, light in the specific wavelength band and excitation light of the phosphor may be coupled into an optical fiber. FIG. 12A shows an excitation spectrum and an emission spectrum under illumination with normal light (illumination by the white illumination light), while FIG. 12B shows an excitation spectrum and an emission spectrum under illumination with special light (illumination by light in the specific wavelength band). As shown in FIG. 12A, the excitation light has a wavelength in an excitation wavelength band W in which the phosphor is excited to emit light, and this excitation light excites the phosphor so as to emit light having a wavelength component indicated by the emission spectrum. However, as shown in FIG. 12B, under the illumination with in the special light, when the light in the specific wavelength band is light having a wavelength within the excitation wavelength band W, unnecessary fluorescence is emitted from the phosphor, and thus an observation image peculiar to the specific wavelength band might not be obtained.

SUMMARY OF THE INVENTION

The invention has been made in view of the above circumstances. The invention provides: a light source device capable of individually picking out light emitted from a phosphor and light in the other wavelength band without mutual interference by only allowing light in a specific wavelength band to excite the phosphor so as to emit light but by causing light in the other wavelength bands to pass through the phosphor without the phosphor being excited to emit light when plural light beams in different wavelength bands pass through the phosphor to obtain outgoing light; an imaging apparatus for detecting light from a light irradiation area by using this light source device; and an endoscope apparatus that is provided with this imaging apparatus and is capable of obtaining a good observation image under plural types of illumination light.

(1) According to an aspect of the invention, a light source device includes a first light source, a second light source and a phosphor. The second light source has an emission wavelength that is different from an emission wavelength of the first light source. The phosphor is disposed to be distant from the first light source and the second light source, and absorbs light in a predetermined excitation wavelength band to emit fluorescence. The phosphor is disposed on an emission light optical path that is shared by the first light source and the second light source. The emission wavelength of the first light source is in the predetermined excitation wavelength band. The emission wavelength of the second light source is outside of the predetermined excitation wavelength band.

With this light source device of (1), when the light from the first light source is irradiated onto the phosphor, the fluorescence is emitted from the phosphor, and when the light from the second light source is irradiated onto the phosphor, the phosphor is not excited to emit light, and the light from the second light source passes therethrough. Therefore, (i) the light from the first light source and the fluorescence emitted from the phosphor and (ii) the light from the second light source can be emitted selectively without mutual interference.

(2) The light source device of (1) may further include an optical fiber that is provided between (i) the first light source and the second light source and (ii) the phosphor.

With this light source device of (2), the light from the first light source and the light from the second light source are irradiated onto the phosphor through the optical fiber. Therefore, an arrangement freedom of both of the respective light sources and the phosphor can be enhanced. Also, since the light sources are connected by the optical fiber having a fine diameter, a connection path can be formed finely.

(3) In the light source device of (2), light obtained by coupling light emitted from the first light source and light emitted from the second light source may be introduced into the optical fiber.

With this light source device of (3), the light from the first light source and the light from the second light source are guided to the phosphor via the single optical fiber. Therefore, the connection path can be narrowed.

(4) In the light source device of any one of (1) to (3), white light may be produced by the fluorescence, which phosphor emits in response to the light emitted from the first light source.

With this light source device of (4), the light emitted from the first light source is irradiated onto phosphor, and then the white light is produced by the fluorescence emitted from the phosphor. Therefore, when a material of the phosphor or the type of the first light source is changed, a light intensity of a desired wavelength component can be easily designed, and the intended white light can be produced simply.

(5) In the light source device of any one of (1) to (4), the first light source may include a blue laser light source that emits a blue laser beam.

With this light source device of (5), an intensity of light per unit area can be increased by using the blue laser light.

(6) In the light source device of any one of (1) to (5), the second light source may include a laser light source that emits a laser beam.

With this light source device of (6), the light in the narrow wavelength band can be emitted.

(7) In the light source device of any one of (1) to (6), the second light source may include a plurality of light sources that have emission wavelengths different from each other.

With this light source device of (7), the light can be emitted from the plurality of light sources, and illumination can be provided in response to a purpose.

(8) The light source device of any one of (1) to (7) may further include a switch that selectively switches between the light from the first light source and the light from the second light source, to irradiate the selected light to the phosphor.

With this light source device of (8), the light from the first light source and the light from the second light source can be switched. Therefore, the light in the different wavelength bands can be emitted selectively.

(9) The light source device of any one of (1) to (8) may further include an excitation light cut filter that is disposed in front of the phosphor on an optical path. The excitation light cut filter absorbs excitation light from the first light source.

With this light source device of (9), the excitation light, which excites the phosphor to emit the light is eliminated on the optical path anterior to the phosphor. Therefore, the emission of the unnecessary light can be eliminated.

(10) In the light source device of any one of (1) to (9), the excitation wavelength band may be defined as that if light having a wavelength in the excitation wavelength band is irradiated onto the phosphor, the irradiated light substantially excites the phosphor.

(11) In the light source device of (10), the excitation wavelength band may be a full width at half maximum of a light emission efficiency of the phosphor.

(12) According to another aspect of the invention, an imaging apparatus includes the light source device according to any one of (1) to (11), and an imaging device. The imaging device includes an imaging element that detects light from a light irradiation area to which the light source device irradiates light, so as to produce an imaging signal.

With this imaging apparatus, the light emitted from the light source device is irradiated onto an object to be inspected, and the light from the object to be inspected can be captured by the imaging element to generate observation image signals of the object to be inspected. Thereby, illumination images generated by the light in the different wavelength bands can be acquired.

(13) In the imaging apparatus of (12), the light emitted from the first light source may have a wavelength that is shorter than a short-wavelength-side detection limit of a spectral sensitivity characteristic of the imaging element.

With this imaging apparatus, the light emitted from the first light source is not detected by the imaging element. Therefore, the process of separating/extracting the light, which is emitted from the first light source, from the image signal, and the like can be omitted simply.

(14) According to further another aspect of the invention, an endoscope apparatus includes the imaging apparatus of any one of (12) to (13), and an endoscope insertion portion. The endoscope insertion portion emits, from a front end thereof, at least one of illumination light from the first light source and illumination light from the second light source.

With this endoscope of (14), different types of illumination lights can be emitted selectively from the front end of the endoscope insertion portion.

(15) In the endoscope apparatus of (14), the light emitted from the second light source may contain at least one of blue light and green light.

With this endoscope apparatus of (15), the blue light and the green light can be emitted. Therefore, a highlighted image in the special light diagnosis can be produced.

(16) In the endoscope apparatus of any one of (14) to (15), the light emitted from the second light source may contain at least one of red light and infrared light.

With the endoscope apparatus of (16), the red light and the infrared light can be emitted. Therefore, observation made in a state where a medicine which can easily absorb the infrared light is injected into the vein, i.e., the infrared light observation and the red fluorescent observation can be carried out.

According to the light source device of any of the above configurations, when plural light beams in different wavelength bands pass through a phosphor to obtain outgoing light, light emitted from the phosphor and light in the other wavelength band can be picked out individually without mutual interference by only allowing light in a specific wavelength band to excite the phosphor so as to emit light but by causing light in the other wavelength bands to pass through the phosphor without the phosphor being excited to emit light.

Also, according to the imaging apparatus of any of the above configurations, an observation image captured by using light emitted from the phosphor as illumination light and observation images captured by using the light in the other wavelength bands as illumination light can be obtained individually.

Furthermore, according to the endoscope apparatus of any of the above configurations, good observation images can be captured under plural types of illumination light, and thus it is possible to make the special light diagnosis with high precision.

BRIEF DESCRIPTION OF THE DRAWINGS

FIG. 10A is an explanatory view conceptually showing a plurality of frame images that are captured in time series by an imaging optical system, and FIG. 10B is an explanatory view conceptually showing a state where these frame images are displayed with being rearranged.

FIG. 12A) and under illumination with special light (illumination by light in a specific wavelength band; FIG. 12B), according to the related art.

DETAILED DESCRIPTION OF EMBODIMENT(S) OF THE INVENTION

A light source device, an imaging apparatus and an endoscope apparatus according to embodiments of the invention will be described based on the endoscope apparatus configured by using the light source device and the imaging apparatus, with reference to the accompanying drawings.
<First Embodiment>

Figure 1:
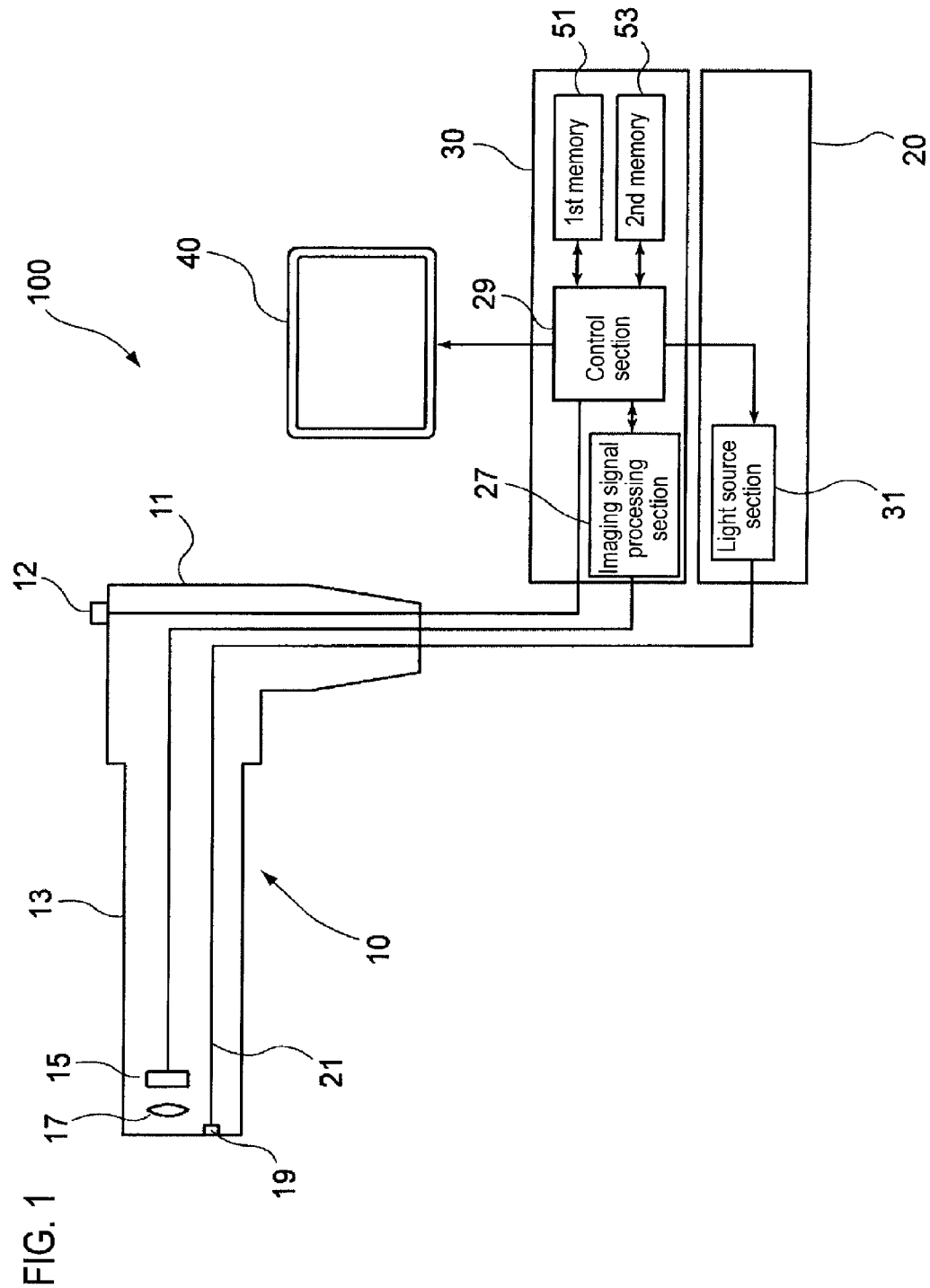
FIG. 1 is a conceptual configuration view of an endoscope apparatus.

FIG. 1 is a conceptual configuration view showing an endoscope apparatus of this embodiment.

An endoscope apparatus 100 of this embodiment is configured to mainly include an endoscope 10, a light source device 20, an image processing device 30, and a monitor 40.

The endoscope 10 has a main body operation portion 11, and an endoscope insertion portion 13 that is connected to the main body operation portion 11 and is inserted into an object to be inspected (body cavity). An imaging element 15 and an imaging lens 17 which serve as an imaging optical system are disposed at the front end portion of the endoscope insertion portion 13. Also, an illumination optical member 19 of an illumination optical system and an optical fiber 21 connected to the illumination optical member 19 are disposed in vicinity of the imaging optical system. The optical fiber 21 is connected to a light source section 31 of the light source device 20 (which will be described in detail later), and an imaging signal from the imaging element 15 is input into the image processing device 30.

As the imaging element 15, an imaging device such as CCD (Charge Coupled Device) or CMOS (Complementary Metal-Oxide Semiconductor) is employed. The imaging signal is converted into image data by an imaging signal processing section 27 based on a command from a control section 29, and appropriate imaging processes are applied to the image data. The control section 29 causes the monitor 40 serving as a captured image displaying unit to display the image data being output from the imaging signal processing section 27, and distributes information containing the image data via the connected network such as LAN (not shown). Also, a first memory 51 and a second memory 53 for storing the imaging signal are connected to the control section 29. The first memory 51 and the second memory 53 will be described later.

Next, a configurative example of the illumination optical system will be explained below.

Figure 2:
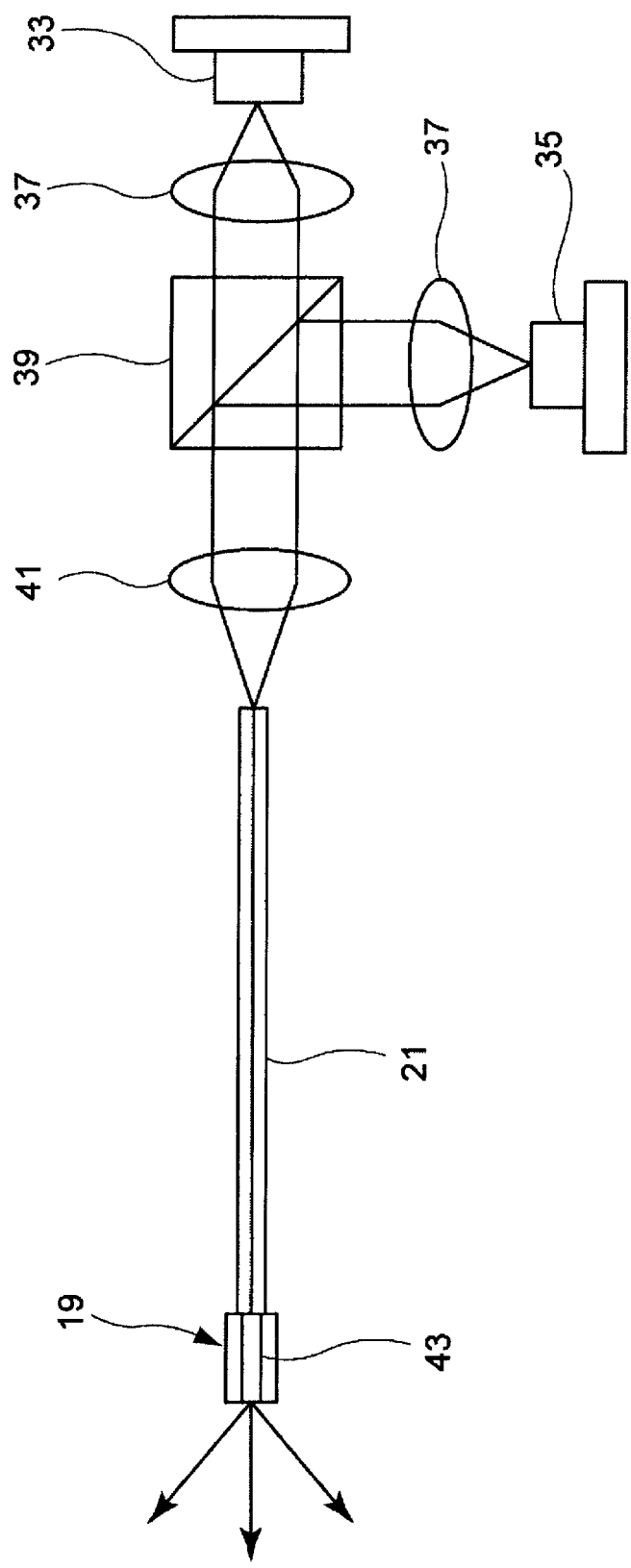
FIG. 2 is a configuration view of an optical system of a light source device shown in FIG. 1.

FIG. 2 is a configuration view showing an optical system of the light source device 20 shown in FIG. 1.

The light source device 20 of this embodiment includes, in the light source section 31, a near-ultraviolet laser light source 33 (an example of a first light source) having a center wavelength of 380 nm, a blue laser light source 35 (an example of a second light source) having a center wavelength of 445 nm, collimator lenses 37, 37 for converting laser beams from the near-ultraviolet laser light source 33 and the blue laser light source 35 into collimated light beams, respectively, a dichroic prism 39 serving as an optical coupling device for polarizing/coupling two laser beams, and a converging lens 41 for converging the laser beams, which are coupled on the same optical axis by the dichroic prism 39, into one end of the optical fiber 21. The illumination optical member 19 on the other end side of the optical fiber 21 is configured to include a phosphor 43 that emits light in response to the laser beam from the near-ultraviolet laser light source 33 as excitation light. The phosphor 43 is disposed in a position that is distant from the near-ultraviolet laser light source 33 and the blue laser light source 35 on an emission light path that is shared by the both light sources. The phosphor 43 absorbs light in a predetermined excitation wavelength band and emits fluorescence. The emission wavelength of the near-ultraviolet laser light source 33 is included in this excitation wavelength band, but the emission wavelength of the blue laser light source 35 is not included therein. Therefore, the phosphor 43 emits the fluorescence in response to the laser beam from the near-ultraviolet laser light source 33. But this phosphor 43 does not emit the fluorescence in response to the laser beam from the blue laser light source 35, and diffuses this laser beam to emit ahead on the optical path. That is, the phosphor 43 emits the blue laser beam as a diffusion beam, which has a diffusion angle of 60° to 70° with respect to an optical axis on one side, from the laser beam having high straightness, and thus emits illumination light without illumination unevenness. In this case, another lens, another filter, etc. may be provided as the illumination optical member 19. Also, the light source section 31 may be disposed in the main body operation portion 11 of the endoscope 10.

The control section 29 controls the emission of the respective laser beams from the near-ultraviolet laser light source 33 and the blue laser light source 35. The near-ultraviolet laser light source 33 emits the near-ultraviolet laser beam while controlling an intensity of the emitted light based on a command from the control section 29. This emergent beam is irradiated onto the phosphor 43 of the endoscope insertion portion 13 through the optical fiber 21.

Here, an InGaN semiconductor laser may be employed as the near-ultraviolet laser light source 33, while an InGaN multi-mode semiconductor laser may be employed as the blue laser light source 35.

As the phosphor 43, for example, a crystalline solid-state fluorescent material that contains lead (Pb) as an additive element and uses calcium digallium tetrasulfide ($CaGa_2S_4$) as a base material or a crystalline solid-state fluorescent material that contains lead (Pb) and cerium (Ce) as additive elements and uses calcium digallium tetrasulfide ($CaGa_2S_4$) as a base material as described in JP 2006-2115 A may be used. With this fluorescent material, the fluorescence that extends over an almost full visible range from about 460 nm to about 660 nm can be obtained, and the color rendering property under illumination with white light can be improved.

Also, $LiTbW_2O_8$ serving as a green phosphor (see Tsutomu Odaki, "Phosphor for White LED", IEICE Technical Research Report ED2005-20, CFM2005-28, SDM2005-28, pp. 69-74 (2005-05), and the like), beta sialon (β-sialon: Eu) blue phosphor (see Naoto Hirosaki, Xie Rong Jun and Ken Sakuma, "New sialon phosphors and white LEDs", Transactions of JSAP, Vol. 74, No. 11, pp. 1449-1452 (2005), or Hajime Yamamoto, School of Bionics, Tokyo University of Technology, Transactions of JSAP, Vol. 76, No. 3, p. 241 (2007)), $CaAlSiN_3$ red phosphor, and the like may be used in combination. The beta sialon is a crystal that is represented by a composition of $Si_{6-z}Al_zO_zN_{8-z}$ (z is a solid soluble amount) in which aluminum and acid are solid-dissolved in a β-type silicon nitride crystal. The phosphor 43 may be formed by mixing $LiTbW_2O_8$, the beta sialon, $CaAlSiN_3$, or may be formed by stacking these phosphors in a layered fashion.

If a selective reflection film for a near-ultraviolet beam for suppressing emission of the unnecessary near-ultraviolet beam is provided to the light emission side of the phosphor 43, the near-ultraviolet beam is incident once again on the phosphor 43, and generation of the fluorescence can be enhanced much more.

The optical fiber 21 is a multi-mode fiber. As an example, a fine cable having 105 μm in core diameter, 125 μm in clad diameter and 0.3 to 0.5 mmφ in outer diameter including a protection layer serving as an outer cover may be employed.

Figure 3A:
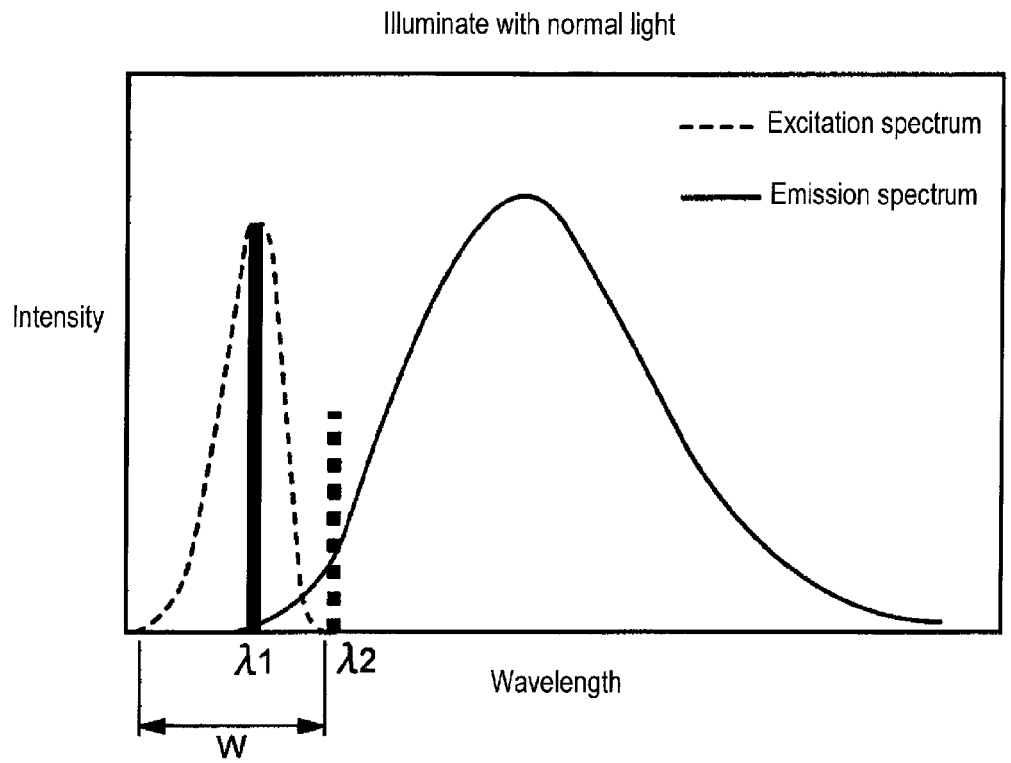
FIGS. 3A and 3B are graphs showing an excitation spectrum, an emission spectrum of a phosphor and spectral intensities of light from respective light sources under illumination with normal light (FIG. 3A) and under illumination with special light (FIG. 3B).
Figure 3B:
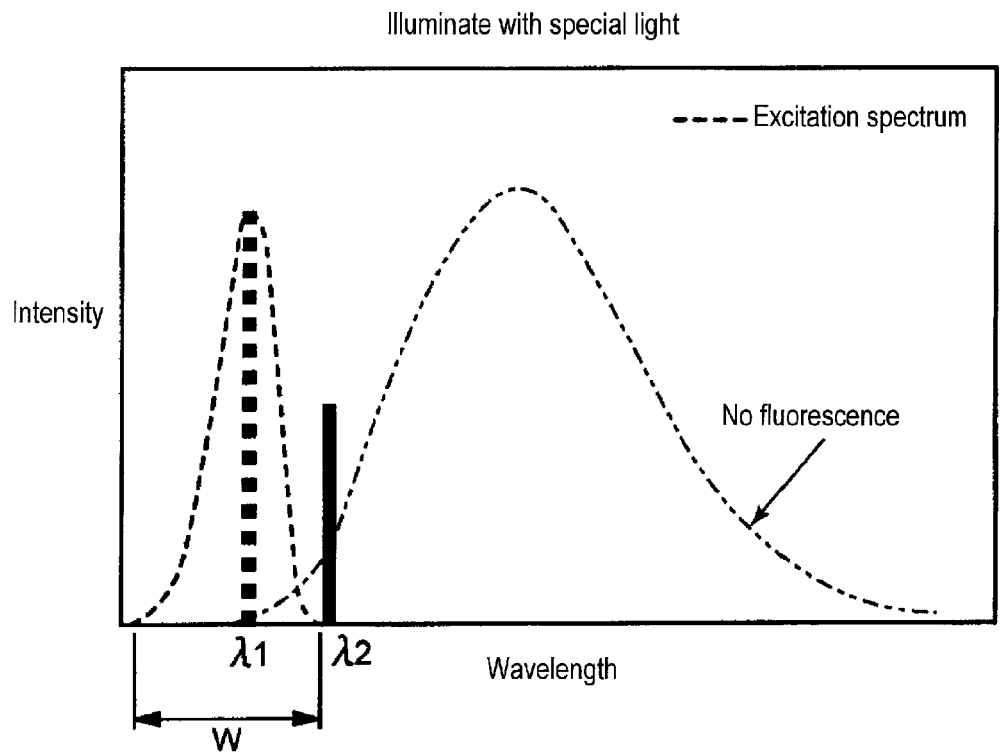

FIGS. 3A and 3B is graphs showing an excitation spectrum and an emission spectrum of a phosphor, and spectral intensities of light from the respective light sources under illumination with normal light (FIG. 3A) and under illumination with special light (FIG. 3B). FIG. 3A is a graph showing a spectral distribution of the fluorescence obtained by wavelength-converting the laser beam from the near-ultraviolet laser light source 33. FIG. 3B is a graph showing a spectral distribution when a laser beam from the blue laser light source 35 is emitted.

As shown in FIG. 3A, the laser beam from the near-ultraviolet laser light source 33 is represented by an emission line at the wavelength $\lambda_1$ (380 nm). The phosphor 43 has a peak of the excitation spectrum at this wavelength $\lambda_1$ (indicated by a broken line in FIG. 3A), and emits the fluorescence (indicated by a solid line in FIG. 3A) at high efficiency. As a result, the laser beam from the near-ultraviolet laser light source 33 is subjected to the wavelength conversion by the phosphor 43, and is emitted as the white beam.

Also, as shown in FIG. 3B, when an output of the near-ultraviolet laser light source 33 is stopped and the blue laser beam at the wavelength $\lambda_2$ (445 nm) is irradiated from the blue laser light source 35 onto the phosphor 43, the phosphor 43 only emits the blue laser beam without emission of the fluorescence because the excitation light is not present in an excitation wavelength band W of the excitation spectrum. That is, when emission light is obtained by causing plural types of light having different wavelengths to pass through the same phosphor 43, only light in the particular wavelength band excites the phosphor 43 so as to emit the fluorescence, but light in the other wavelength bands do not excite the phosphor 43 so as to emit fluorescence and passes through the phosphor 43. As a result, the light (fluorescence) emitted from the phosphor 43 and the light in the other wavelength bands can be picked out individually without mutual interference.

Next, an example using the endoscope apparatus 100 into which the light source device 20 configured as above is incorporated will be described below.

As shown in FIG. 1, the endoscope insertion portion 13 of the endoscope apparatus 100 is inserted into the body cavity, and the white illumination light and the special color illumination light are emitted from the front end of the endoscope insertion portion 13 through the illumination optical member 19. Then, the control section 29 switches between the white light and the special color light, and only either of the both light is emitted. Then, this emission light is irradiated onto an object to be inspected, and then the reflected light is captured by the imaging element 15 through the imaging lens 17. The imaging signal processing section 27 performs the appropriate imaging process for the captured imaging signal, and then the resultant signal is output to the monitor 40 or stored in a recording medium.

During the capturing operation by using the imaging element 15, in the normal endoscope diagnosis in which observation is performed while irradiating the white illumination light to the body cavity, the control section 29 turns on an output of the near-ultraviolet laser light source 33 and turns off an output of the blue laser light source 35. In this case, the fluorescence emitted from the phosphor 43, which is excited in response by the laser beam from the near-ultraviolet laser light source 3, that is, the white illumination light, is irradiated onto the object to be inspected. Also, in the special light diagnosis of the endoscope apparatus 100, the control section 29 turns on the output of the blue laser light source 35 and turns off the output of the near-ultraviolet laser light source 33. In this case, the blue light from the blue laser light source 35 in a narrow wavelength band is irradiated onto the object to be inspected.

Then, the imaging element 15 captures the light reflected from the object to which the blue light is irradiated, and the imaging signal processing section 27 causes the monitor 40 to display image information for the special light diagnosis. As the image information at this time, an observation image obtained by the blue laser beam may be displayed or a quasi-color image produced by using the observation image obtained by other illumination light may be displayed. Details of the image processing in the special light diagnosis mode will be described later.

With this configuration, the control section 29 switches between the respective outputs of the near-ultraviolet laser light source 33 and the blue laser light source 35. Therefore, the normal light illumination in which the white light is irradiated as shown in FIG. 3A and the special light illumination in which the light in the specific wavelength band is irradiated as shown in FIG. 3B can be provided selectively. With the normal light illumination, an observation image having a similar color tone to that obtained when the image is observed with the naked eye can be obtained. Also, with the special light illumination, a diagnosis image used in the special light diagnosis can be obtained.

Also, when the white light is irradiated, the light from the near-ultraviolet laser light source 33 serving as the excitation light is not involved in the captured image, and thus the unnecessary light is never mixed. Also, an object to be inspected is illuminated by the wide-band continuous spectrum, which has high light intensities from the shorter wavelength side being close to the excitation light. Therefore, the color rendering property can be improved without lack of the spectral intensity in the specific wavelength band (for example, the blue wavelength band as in the related art). As a result, a color reproducibility of the white illumination image can be improved, overlooking of a lesion part in the endoscope diagnosis can be reduced, and this configuration can contribute to an improvement of diagnosis accuracy.

Also, the white illumination light and the light in the particular narrow visible wavelength band may be switched by a simple handy operation such as a switch 12 provided in the main body operation portion 11 of the endoscope 10, or the like. In this case, the illumination light can be switched manually at any timing, and usability can be improved.

Here, the phosphor 43 of this embodiment has such a characteristic that it is excited by the light of the wavelength $\lambda_1$ emitted from the near-ultraviolet laser light source 33 and is not excited by the light of the wavelength $\lambda_2$ emitted from the blue laser light source 35. As the phosphors having such characteristic, materials shown in FIG. 4 may be employed in addition to the above ones.

Figure 4A:
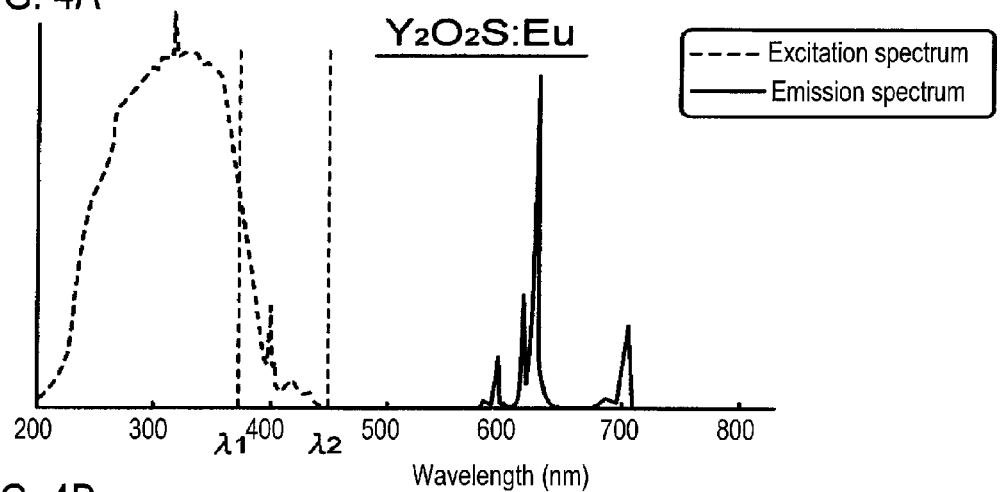
FIGS. 4A to 4D are graphs showing excitation spectrums and emission spectrums of respective phosphors, each of which has such a characteristic that each phosphor is excited by light of wavelength $\lambda_1$ emitted from a near-ultraviolet laser light source but is not excited by light of wavelength $\lambda_2$ emitted from a blue laser light source.
Figure 4B:
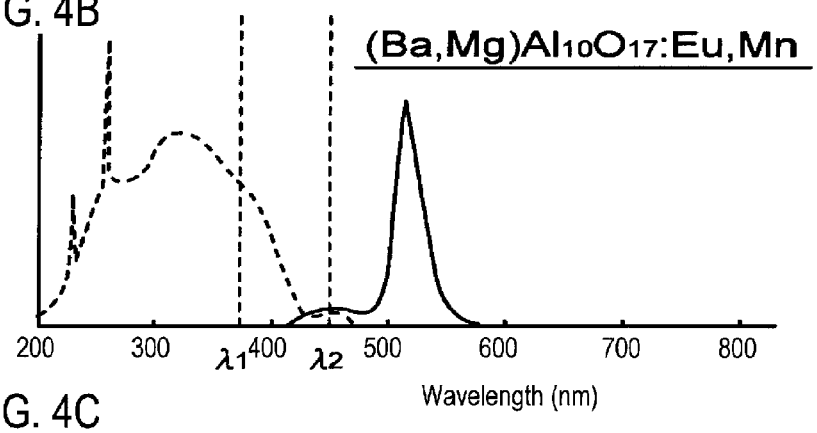
Figure 4C:
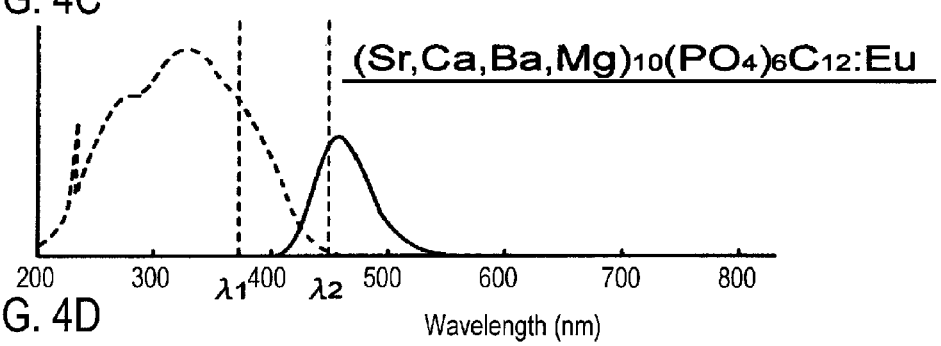
Figure 4D:
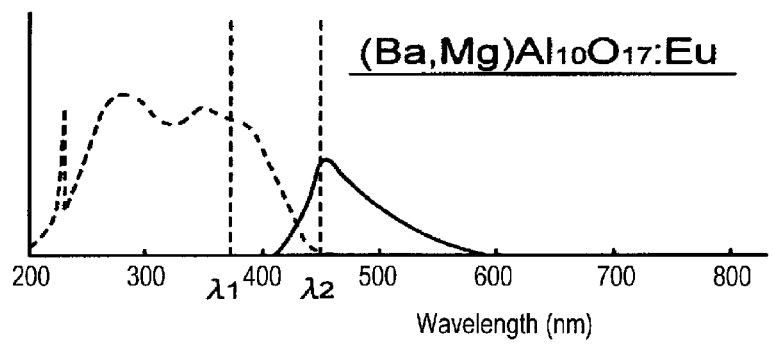

FIGS. 4A to 4D shows the excitation spectrums and the emission spectrums of respective phosphors, wherein FIG. 4A shows a red light emitting phosphor of $Y_2O_2S$:Eu, FIG. 4B shows a green light emitting phosphor of $(Ba, Mg)Al_{10}O_{17}$: Eu, Mn, FIG. 4C shows a blue light emitting phosphor of $(Sr, Ca, Ba, Mg)_{10}(PO_4)_6C_{12}$:Eu, and FIG. 4D shows a blue light emitting phosphor of $(Ba, Mg)Al_{10}O_{17}$:Eu. All phosphors are hardly excited by the light of the wavelength $\lambda_2$, and are excited by the light of the wavelength $\lambda_1$.

Here, the property that the phosphors exemplified above are excited by the near-ultraviolet laser beam from the near-ultraviolet laser light source 33 and are not excited by the blue laser beam from the blue laser light source 35 so as to emit the light, i.e., emission wavelengths of the other light sources are not included in the excitation wavelength band peculiar to the phosphor, may be defined in detail as follows.

The excitation spectrum of the phosphor exists over the specific wavelength band. If a wavelength in a range in which a luminous efficiency of the excitation spectrum is high is used as the excitation light, the fluorescence can be emitted at a high efficiency. Therefore, it is preferable in this embodiment that the near-ultraviolet laser beam has a wavelength whose luminous efficiency is high in the excitation spectrum of the phosphor. In contrast, the blue laser beam in this embodiment is set to have the wavelength whose luminous efficiency in the excitation spectrum is low.

The excitation spectrum of the phosphor has such a profile that one or plural peaks appear and its luminous efficiency is gradually lowered as a wavelength becomes distant from the wavelength at which the maximum luminous efficiency appears. If a wavelength range that is expanded until a foot of the peak becomes completely zero is set as the excitation wavelength band in the profile having the peaks, such an excitation wavelength band would be a considerably wide wavelength band. In this case, even if light having a wavelength corresponding to the foot of the peak is irradiated onto the phosphor, fluorescence emitted would be weak. For this reason, the excitation wavelength band in which excitation is substantially caused may be defined as a wavelength band of a full width at half maximum of the luminous efficiency. Also, preferably the excitation wavelength band is set to be a wavelength band that has luminous efficiencies up to 1/10 of the maximum luminous efficiency, more preferably the excitation wavelength band is set to be a wavelength band that has luminous efficiencies up to 1/100 of the maximum luminous efficiency. Further, when the excitation wavelength band is set to be a wavelength band that has luminous efficiencies up to 1/1,000 of the maximum luminous efficiency, unnecessary fluorescent components can be eliminated with high accuracy.

Figure 12A:
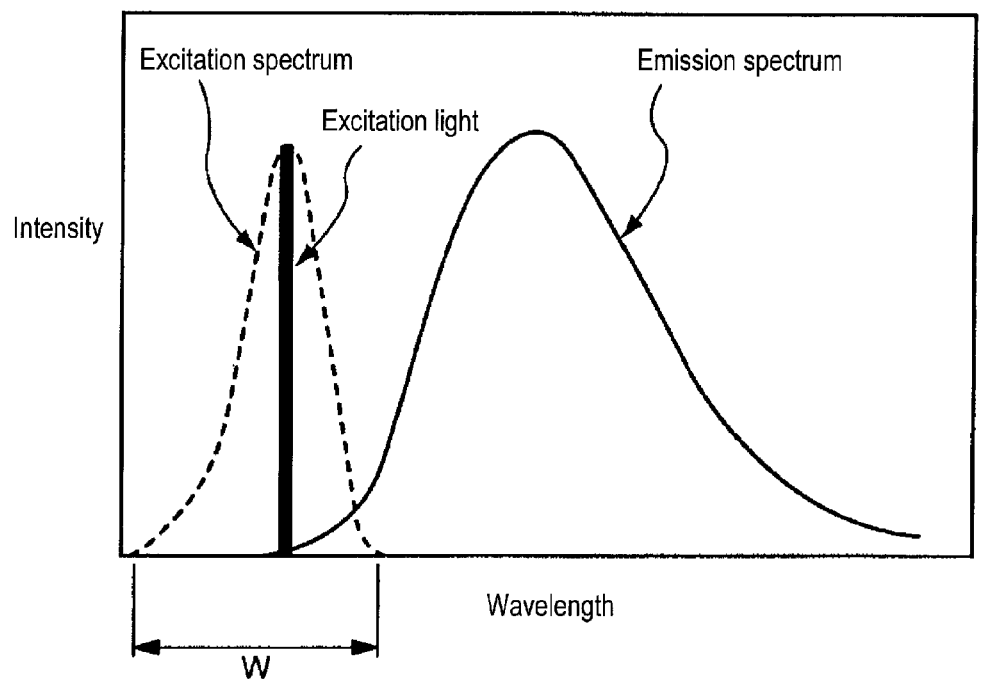
FIGS. 12A and 12B are graphs showing an excitation spectrum and emission spectrums under illumination with normal light illumination (illumination by white illumination light.
Figure 12B:
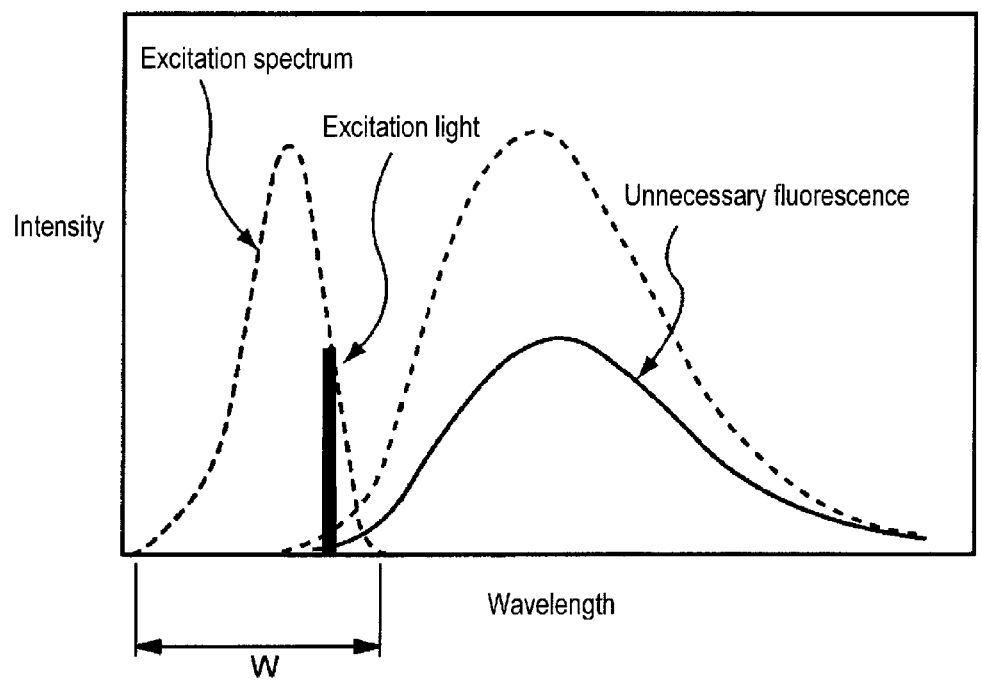

Also, the excitation wavelength band may be defined based on the emission spectrum of the phosphor. For example, in terms of a relationship between an integral intensity $I_1$ of the emission spectrum of the phosphor shown in FIG. 12A and an integral intensity $I_2$ of the emission spectrum of the unnecessary fluorescence shown in FIG. 12B, the excitation wavelength band may be defined as having 50% or less in ratio of the integral intensity $I_2$ to the integral intensity $I_1$, preferably 10% or less, more preferably 1% or less, and further preferably 0.1% or less.

In any event, a range of the excitation wavelength band may be set in accordance with various conditions such as an object to be illuminated, a purpose, an employed phosphor, and the like.

<Second Embodiment>

Next, a light source device according to another embodiment will be described below.

Figure 5:
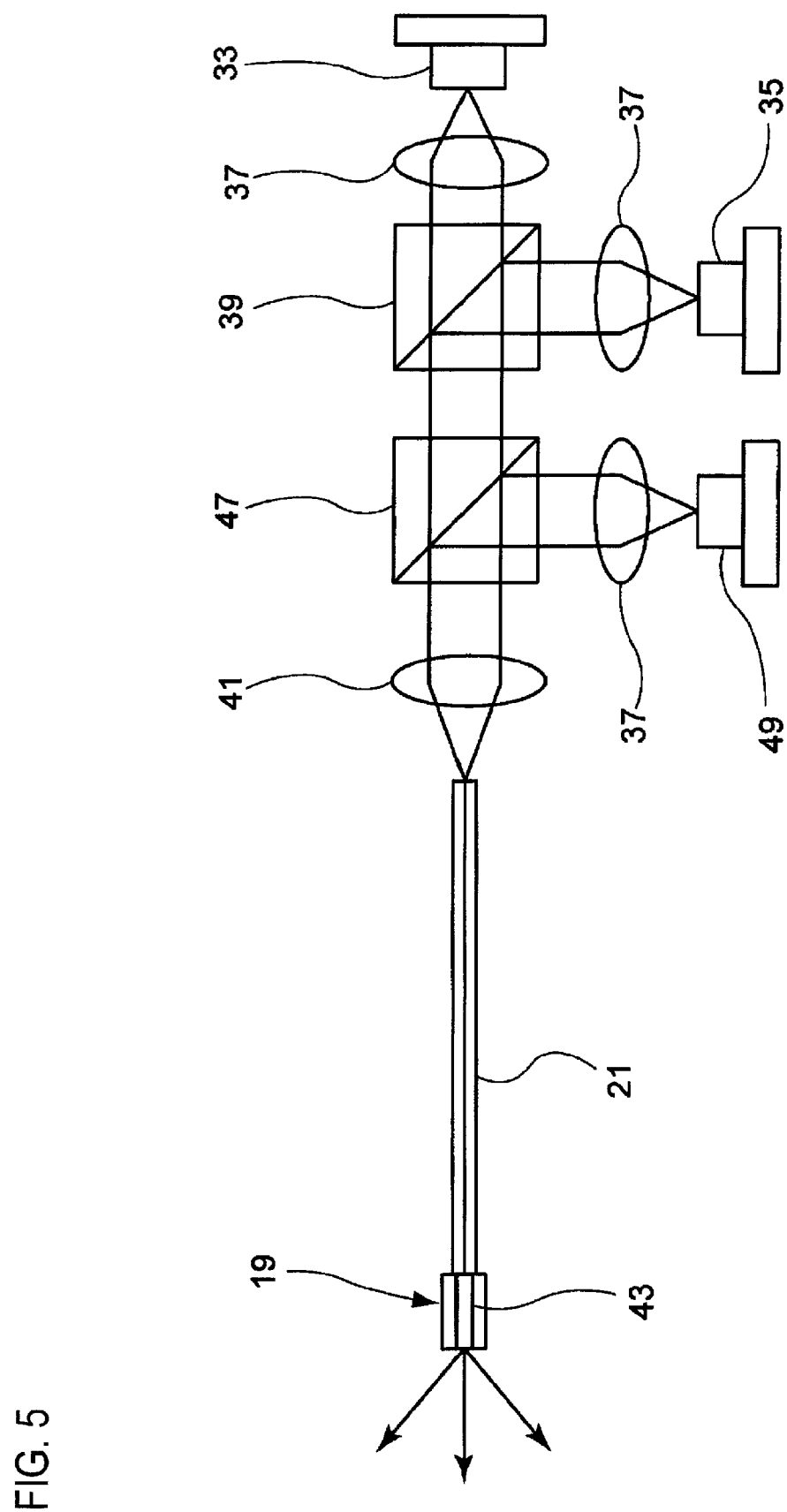
FIG. 5 is a configuration view of another optical system of the light source device shown in FIG. 1.

FIG. 5 is a configuration view showing another optical system of the light source device shown in FIG. 1. Here, the same reference symbols are affixed to the same members as those shown in FIG. 2, and explanation thereon will be omitted or simplified.

This embodiment is configured so that the optical system shown in FIG. 2 can emit a green laser beam. That is, as shown in FIG. 5, a dichroic prism 47 for introducing a green laser beam is disposed in front of the emission optical path of the dichroic prism 39 for introducing the blue laser emitted from the blue laser light source 35. A green laser beam emitted from a green laser light source 49 is introduced into this dichroic prism 47 via the collimator lens 37.

As the green laser light source 49, a YAG-SHG laser whose center wavelength is 532 nm may be used.

The green laser beam from the green laser light source 49 is coupled to the optical paths of the respective laser beams from the near-ultraviolet laser light source 33 and the blue laser light source 35, and then introduced into the optical fiber 21 via the converging lens 41. The phosphor 43 disposed on the light emission side of the optical fiber 21 is not excited by the introduced green laser beam, but is only excited by the near-ultraviolet laser beam from the near-ultraviolet laser light source 33 as in the first embodiment.

Figure 6A:
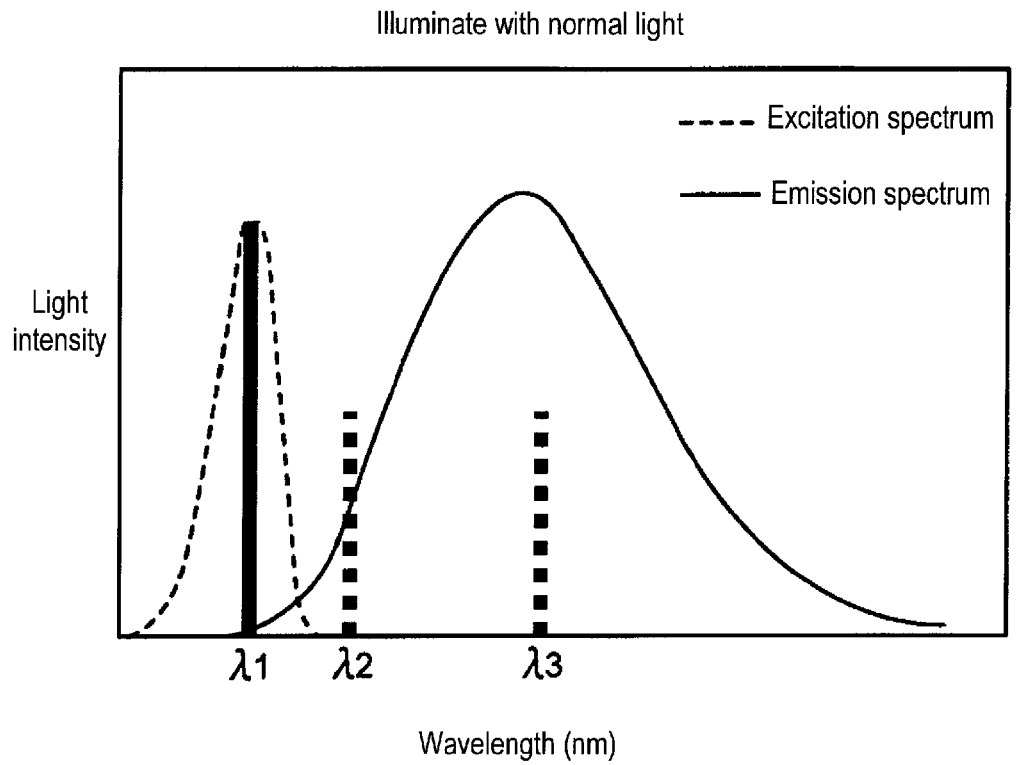
FIGS. 6A and 6B are graphs showing an excitation spectrum, an emission spectrum of a phosphor and spectral intensities of light from respective light sources under illumination with normal light (FIG. 6A) and under illumination with special light (FIG. 6B).
Figure 6B:
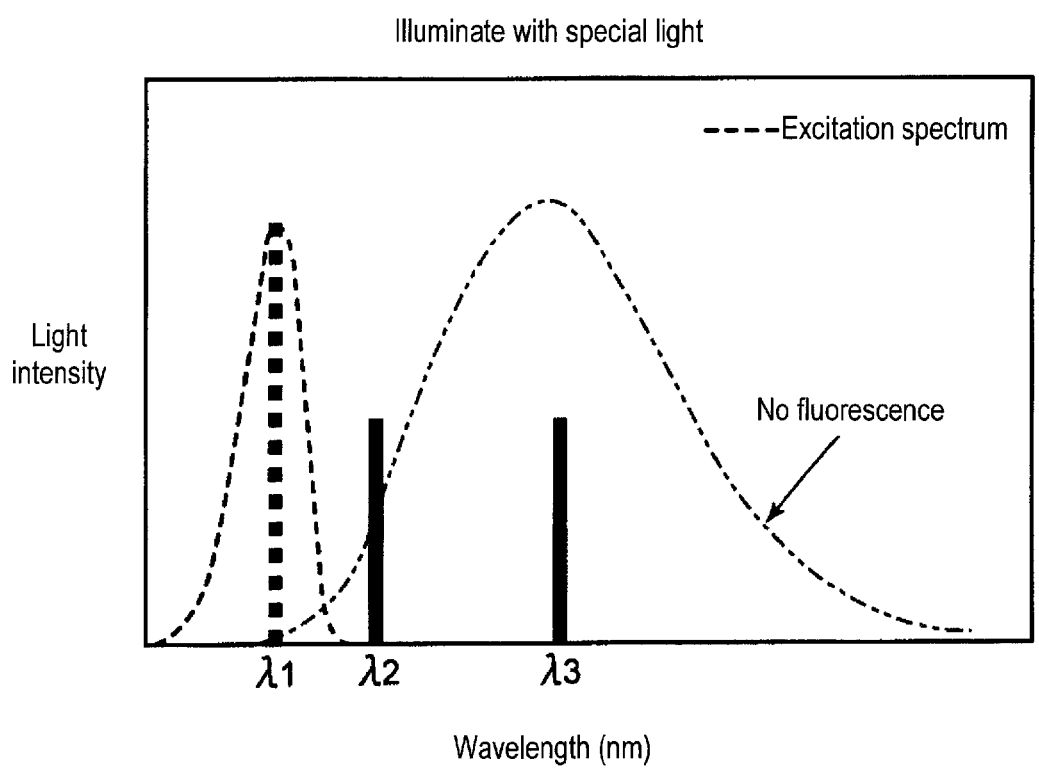

FIGS. 6A and 6B are graphs showing an excitation spectrum, an emission spectrum of a phosphor and spectral intensities of light from respective light sources under illumination with normal light (FIG. 6A) and under illumination with special light (FIG. 6B). As shown in FIG. 6A, in the normal light illumination in which the white light is irradiated, the white light is output from the phosphor 43, which is excited by the near-ultraviolet laser beam from the near-ultraviolet laser light source 33. As shown in FIG. 6B, in the special light illumination in which the special light is irradiated, the blue laser beam from the blue laser light source 35 and the green laser beam from the green laser light source 49 are output. In this case, both outputs of the blue laser light source 35 and the green laser light source 49 may turned ON, and alternatively, only one of the both outputs may be turned ON.

In this manner, the white light, the blue light in a narrow wavelength band and the green light in a narrow wavelength band can be irradiated selectively. Therefore, an observation image captured by using the white light, which has the enhanced color rendering property and an observation image for the special light diagnosis captured by using the blue light and the green light in the narrow wavelength bands can be obtained without mutual interference. As a result, for example, pits and surface blood vessels can be depicted by the blue laser beam whose center wavelength is 445 nm, and also fine blood vessels and flushes in a deep part can be observed by the green laser beam whose center wavelength is 532 nm. Also, a quasi-color image for the special light diagnosis can be produced by using these observation images. For example, green detection signals (reflected light component of the green light in the narrow band) obtained by the imaging element 15 when the blue light and the green light in the narrow wavelength band are irradiated are converted into a red color tone and also blue detection signals are converted into blue and green color tones. Thereby, the quasi-color image is produced. With this quasi-color image, the surface fine structures (capillary vessels, mucosal fine structures, etc.) in the surface layer of the object to be inspected can be observed clearly.

<Third Embodiment>

Next, a third embodiment that is configured so that the spectral characteristic of the imaging element is correlated with the light source wavelength of the illumination optical system will be described below.

The light source of this embodiment has basically the similar configuration to that in the first embodiment, but a relationship between the imaging element and the light source that excites the phosphor is defined in this embodiment.

Figure 7:
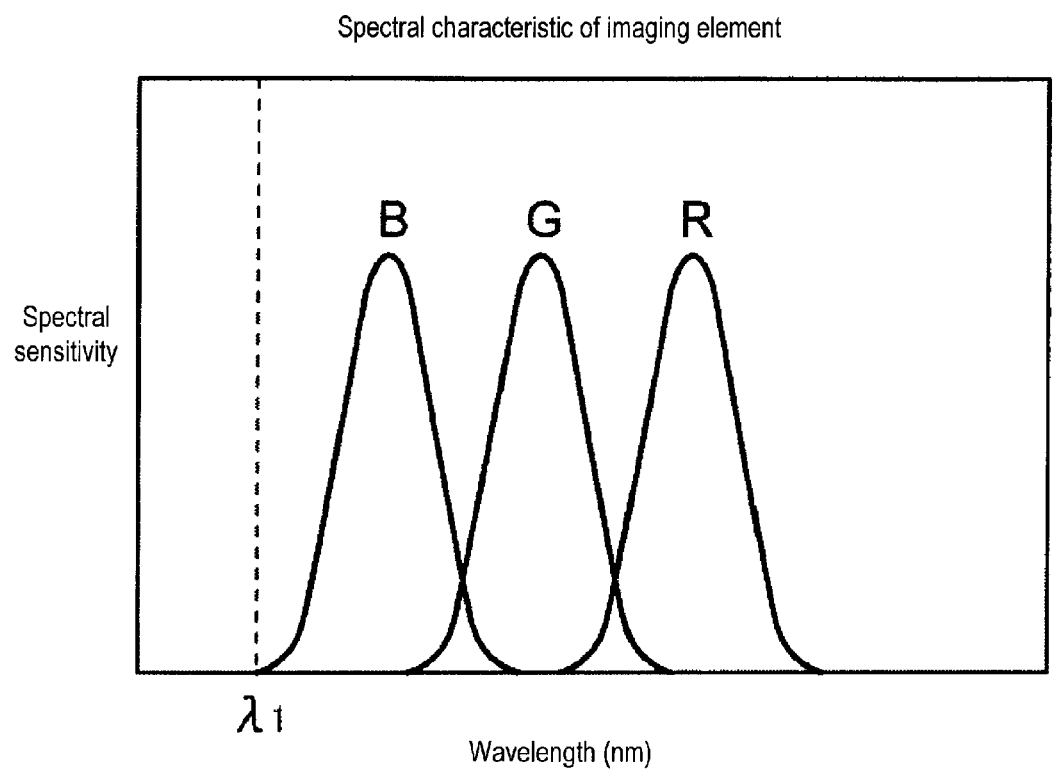
FIG. 7 is a graph showing a spectral characteristic of an imaging element.

The imaging element 15 of this embodiment (see FIG. 1) has R (red), G (green), and B (blue) detection spectral characteristics as shown in FIG. 7. In this case, the spectral sensitivity for blue that is the detection color on the shortest wavelength side is set not to include the emission wavelength $\lambda_1$ of the near-ultraviolet laser light source. As a result, the light emitted from the near-ultraviolet laser light source, which excites the phosphor 43 to emit light, is not detected by the imaging element 15.

That is, the emission wavelength of the light source, which excites the phosphor 43 to emit light, is set to a wavelength that is shorter than a detection limit on the shorter wavelength side in the spectral sensitivity characteristics of the imaging element 15. Therefore, the light from the near-ultraviolet laser light source 33, which provides the excitation light for the phosphor, does not exert influence on an observation image (captured image) at all. As a result, even when an output of the near-ultraviolet laser light source 33 is changed, no change is caused in the color tone of the fluorescence that the phosphor 43 emits, and also the observation image illuminated always in a constant color tone can be obtained. Also, the diagnosis accuracy can be improved much more.

<Fourth Embodiment>

Next, a fourth embodiment including an unnecessary light cut filter for removing light used to excite the phosphor so as to emit fluorescence after the excitation light is irradiated onto the phosphor will be described below.

Figure 8:
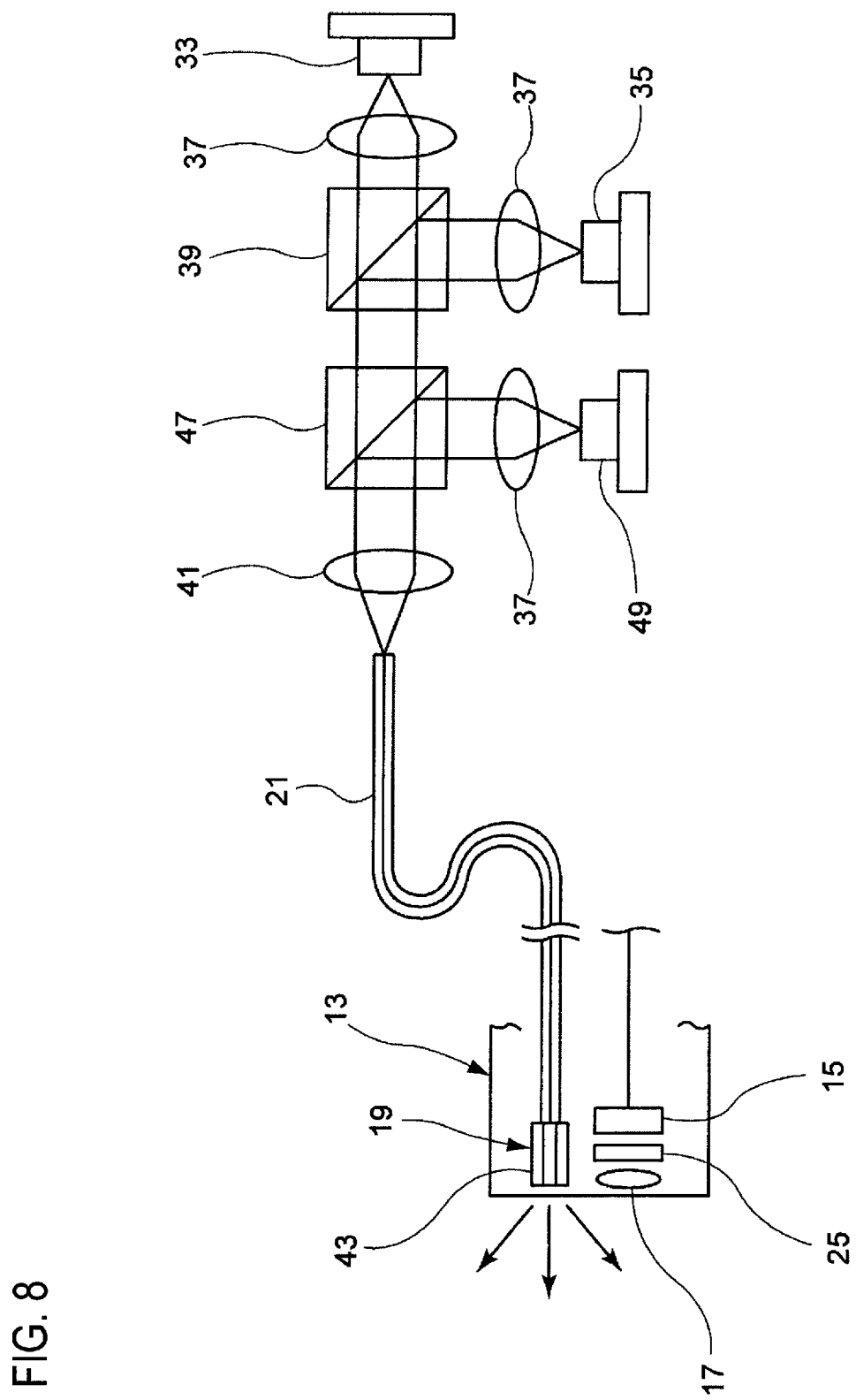
FIG. 8 is a configuration view of still another optical system.

FIG. 8 is a configuration view showing still another optical system. Here, the same reference symbols are affixed to the same members as those shown in FIG. 5, and explanation thereon will be omitted or simplified.

Figure 9:
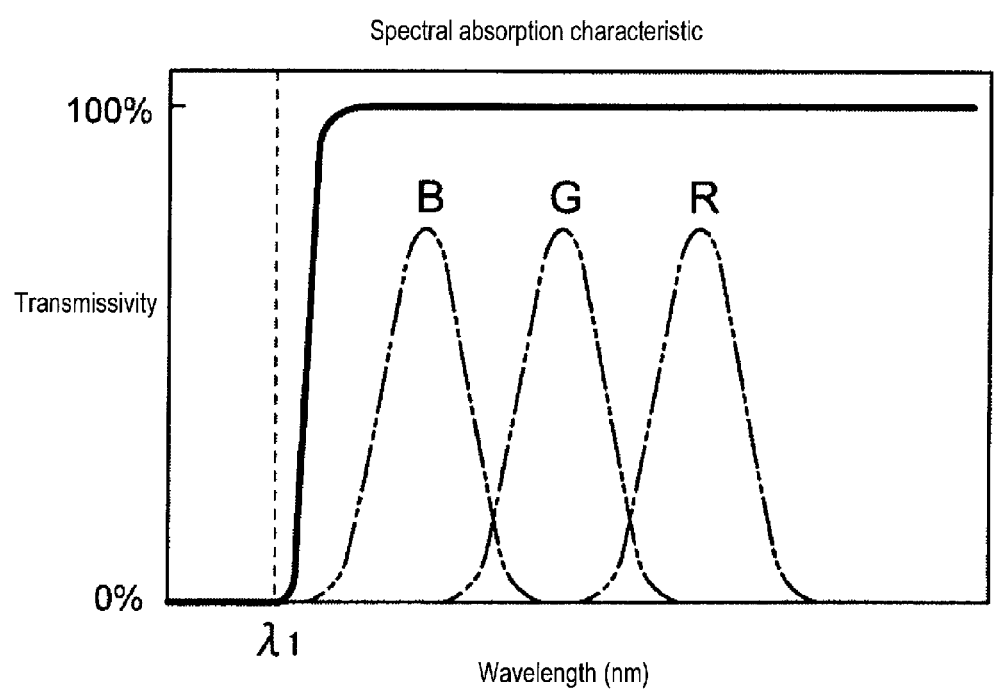
FIG. 9 is a graph showing a spectral absorption characteristic of an unnecessary light cut filter.

In the imaging optical system of this embodiment, an unnecessary light cut filter 25 is disposed between the imaging element 15 and the imaging lens 17 of the endoscope insertion portion 13. The unnecessary light cut filter 25 is an optical filter having a spectral absorption characteristic shown in FIG. 9. That is, the unnecessary light cut filter 25 has such a characteristic that it absorbs the wavelength $\lambda_1$ component of the light, which excites the phosphor 43 to emit light, and allows the light component of the wavelength longer than the wavelength $\lambda_1$ to pass therethrough.

With the unnecessary light cut filter 25 having the spectral absorption characteristic, like the third embodiment, the light from the near-ultraviolet laser light source 33, which serves as the excitation light of the phosphor, does not exert influence upon an observation image (captured image) at all. Also, when this unnecessary light cut filter 25 is disposed anterior to the phosphor 43 of the illumination optical system on the optical path, it can be prevented that the unnecessary near-ultraviolet laser beam is irradiated onto the object to be inspected, and cells, etc. of the object can be prevented from being subject to biological damage, and the like.

<Image Processing Method>

Next, an example of use of the endoscope apparatus in the special light diagnosis, and an example of image processing performed for an acquired observation image of the endoscope apparatus in the respective embodiments will be described below.

FIG. 10A is an explanatory view conceptually showing a plurality of frame images that are captured in time series by the imaging optical system, and FIG. 10B is an explanatory view conceptually showing a state where these frame images are displayed with being rearranged. Here, it is assumed that an observation image that is captured under illumination with the white light and an observation image that is captured under illumination with the light in the particular visible wavelength band are displayed separately on the monitor 40.

As shown in FIG. 10A, the control section 29 (see FIG. 1) controls the emission light from the light source device 20 so that the light source device 20 emits the near-ultraviolet laser beam having the center wavelength of 380 nm at the first frame to irradiate the white light onto the object to be inspected. The imaging element 15 captures an image of the object that is irradiated by the white light, and stores the imaging signal in the first memory 51 shown in FIG. 1.

Then, the control section 29 controls the emission light from the light source device 20 so that the light source device 20 emits the blue laser beam of the center wavelength 445 nm and the green laser beam of the center wavelength 532 nm at the second frame. The imaging element 15 captures an image of the object that is irradiated by the light beams in the respective wavelengths, and stores the imaging signals in the second memory 53.

Figure 11:
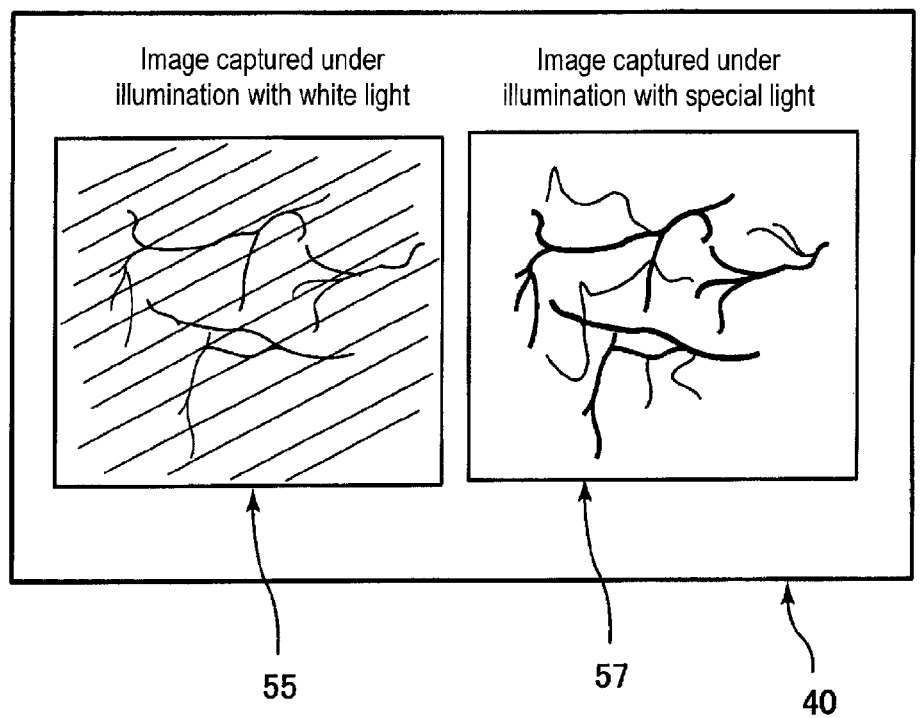
FIG. 11 is an explanatory view showing a state where plural types of image information are displayed in different display areas on a monitor.

Subsequently the processes of irradiating/imaging/storing an imaging signal are repeated similarly at the third frame (odd-numbered frame) like the first frame and the fourth frame (even-numbered frame) like the second frame, respectively. That is, the illumination with the white light and the illumination with light including the light in the particular visible wavelength band are switched alternatively every imaging frame of the imaging element 15. Then, as shown in FIG. 10B, the observation image captured by the white light is stored in the first memory 51, and the observation image captured by the light in the particular visible wavelength band, i.e., the image for the special light diagnosis, is stored in the second memory 53. Then, as shown in FIG. 11, the imaging signals stored in the first memory 51 and the second memory 53 are displayed in different display areas 55, 57 on the monitor 40 as image information given by two types of imaging signals. Sizes of both display areas are set to be identical in the illustrated example. However, a display fashion may be set arbitrarily, e.g., one display area may be set to be larger than the other display area, an image in one display area may be displayed over the other display area, or the like.

In this case, the above example is just an example. For example, the displaying sequence may also be set arbitrarily, e.g., an image captured when the blue laser beam is irradiated may be set at the second frame, an image captured when the green laser beam is irradiated may be set at the third frame, and the like.

Also, an image captured under illumination with the white light at the first frame may be superposed on images captured under illumination with the special light at the second frame and the third frame, and then the superposed image may be displayed on the monitor 40. For example, when an image captured under illumination with the special light is mixed in a part of an area of an image captured under illumination with the white light illumination, a part to be observed may be displayed as a highlighted image (quasi-color image), and also a surrounding image may be displayed simultaneously as an image captured under illumination with the white light. As a result, an operator can make easily diagnosis while grasping precisely a position of the object to be observed. Also, since the images at the respective frames are superposed and displayed simultaneously, frame dropping can be made inconspicuous when a moving image is displayed.

In this manner, the image captured under illumination with the white light and the image captured under illumination with light including the light in the particular visible wavelength band are acquired alternately. Therefore, the both images can be acquired substantially simultaneously, and also plural types of image information can be simultaneously displayed in real time. Also, respective pieces of image information may be displayed side by side. Therefore, the operator can simultaneously grasp an observation position and the properties of the part to be observed, and also diagnosis accuracy in the special light diagnosis can be enhanced much more.

Also, respective detection light screens at respective frames obtained by the imaging may be combined with each other appropriately and utilized. Thereby, image information that is convenient for diagnosis can be provided simply. For example, easily obtained is an image clearly showing (i) capillary vessels in a surface part of tissue being captured by blue light that hardly reaches a deep part of mucosa and (ii) blood vessels in the deep part being captured by green light that reaches an inside of the tissue Also, when infrared light is used as light in the particular visible wavelength band, an infrared observation can be done. For example, when ICG (indocyanine green), which easily absorbs infrared light, is injected into the vein and then the infrared light is irradiated, information that is difficult for the human eye to view can be observed with emphasis, and the deep-part blood vessel can be observed.

Also, thickening that is diagnosed based on the infrared fluorescent observation can be observed based on the self-emission of the phosphor such as collagen, or the like. At that time, the green light or the blue light is employed as the excitation light.

As explained above, according to the endoscope apparatus 100 of this embodiment, the laser beam is employed as the white light source of the illumination optical system, and thus the light can be guided by the optical fiber and a high-intensity light can be propagated at high efficiency while suppressing diffusion. Also, the optical waveguide for the white color can be configured by the optical fiber, and thus a finer diameter of the endoscope insertion portion can be easily attained without a light guide (optical fiber bundle) of the related art. That is, in order to guide the required light to the front end of the endoscope insertion portion 13 via the light guide, a diameter of at least about 1 mm or more is required of the light guide. In the configuration of this embodiment using a single-core optical fiber, an outer diameter including a protection material of the outer cover can be reduced to a fine diameter of about 0.3 mm. Also, in contrast to the case where the light in a narrow wavelength band is picked out by filtering light from the xenon lamp that is commonly used in the endoscope filed, an equivalent brightness can be realized by a power consumption of about 1/20. Further, since waste heat can be reduced, a size reduction and silencing of a cooling fan, and the like can be attained.

The light source device, the imaging apparatus and the endoscope apparatus using the same are not limited to the above embodiments. Modification, improvement, etc. can be made thereto appropriately. Also, it is needless to say that the endoscope apparatus can be utilized in any other applications including the industrial endoscope other than the application in the medical endoscope. Also, the light source device and the imaging apparatus can be applied for a wide variety of purposes.

What is claimed is:

1. An imaging apparatus, comprising:
a light source device;
an imaging device including an imaging element that detects light from a light irradiation area to which the light source device irradiates light, so as to produce an image signal;
a first light source;
a second light source having emission wavelengths that are different from an emission wavelength of the first light source, wherein the second light source includes a plurality of light sources that have the emission wavelengths different from each other;
a phosphor that is disposed to be distant from the first light source and the second light source and absorbs light in a predetermined excitation wavelength band to emit fluorescence;
a control section that controls the first light source and the second light source,
wherein the phosphor is disposed on an emission light optical path that is shared by the first light source and the second light source,
wherein the emission wavelength of the first light source is in the predetermined excitation wavelength band,
wherein the emission wavelengths of the second light source are outside of the predetermined excitation wavelength band,
wherein the control section switches between an emission of the first light source and an emission of the second light source, in every imaging frame of the imaging device,
wherein light emitted from the second light source includes blue light, and
wherein the emission light optical path shared by the first light source and the second light source comprises a single-core optical fiber;
a dichroic prism for coupling light emitted from the first light source and the light emitted from the second light source into the single-core optical fiber;
a converging lens for converging the light emitted from the first light source and the light emitted from the second light source, which are coupled on a same optical axis by the dichroic prism, into one end of the single-core optical fiber; and
an illumination optical member located on another end of the single-core optical fiber for holding the phosphor.

2. The imaging apparatus according to claim 1, wherein the single-core optical fiber that is provided between (i) the first light source and the second light source and (ii) the phosphor.

3. The imaging apparatus according to claim 2, wherein light obtained by coupling light emitted from the first light source and the light emitted from the second light source is introduced into the optical fiber.

4. The imaging apparatus according to claim 1, wherein white light is produced by the fluorescence, which the phosphor emits in a response to light emitted from the first light source.

5. The imaging apparatus according to claim 1, wherein the first light source includes a blue laser light source that emits a blue laser beam.

6. The imaging apparatus according to claim 1, wherein the second light source includes a laser light source that emits a laser beam.

7. The imaging apparatus according to claim 1, further comprising:
an excitation light cut filter that is disposed in front of the phosphor on an optical path, the excitation light cut filter that absorbs excitation light from the first light source.

8. The imaging apparatus according to claim 1, wherein the excitation wavelength band is defined as that if light having a wavelength in the excitation wavelength band is irradiated onto the phosphor, the irradiated light substantially excites the phosphor.

9. The imaging apparatus according to claim 8, wherein the excitation wavelength band is a full width at half maximum of a light emission efficiency of the phosphor.

10. The imaging apparatus according to claim 1, wherein light emitted from the first light source has a wavelength that is shorter than a short-wavelength-side detection limit of a spectral sensitivity characteristic of the imaging element.

11. An endoscope apparatus comprising:
the imaging apparatus according to claim 1; and
an endoscope insertion portion that emits, from a front end thereof, at least one of illumination light from the first light source and illumination light from the second light source.

12. The endoscope apparatus according to claim 11, wherein the light emitted from the second light source further includes green light.

13. The endoscope apparatus according to claim 11, wherein the light emitted from the second light source further comprises at least one of red light and infrared light.

* * * * *